United States Patent
Guenter et al.

(10) Patent No.: US 8,181,773 B2
(45) Date of Patent: May 22, 2012

(54) CONTAINER FOR A MEDICAL INSTRUMENT OR IMPLANT, IN PARTICULAR A DENTAL INSTRUMENT OR A DENTAL IMPLANT

(75) Inventors: Daniel Guenter, Basel (CH); Rainer Bammerlin, Basel (CH)

(73) Assignee: Straumann Holding AG, Basel (CH)

( * ) Notice: Subject to any disclaimer, the term of this patent is extended or adjusted under 35 U.S.C. 154(b) by 4 days.

(21) Appl. No.: 12/843,221

(22) Filed: Jul. 26, 2010

(65) Prior Publication Data

US 2011/0017622 A1 Jan. 27, 2011

(30) Foreign Application Priority Data

Jul. 27, 2009 (EP) .................................... 09009674

(51) Int. Cl.
*A61B 19/02* (2006.01)
(52) U.S. Cl. ...................... 206/63.5; 206/368
(58) Field of Classification Search ................. 206/63.5, 206/368, 369, 438; 220/8; 433/172–174, 433/167
See application file for complete search history.

(56) References Cited

U.S. PATENT DOCUMENTS

| | | | | |
|---|---|---|---|---|
| 5,062,800 A | * | 11/1991 | Niznick | ......................... 206/368 |
| 5,509,530 A | * | 4/1996 | Wilson | ......................... 206/63.5 |
| 5,733,124 A | | 3/1998 | Kwan | |
| 6,247,932 B1 | * | 6/2001 | Sutter | ........................... 433/173 |
| 6,913,465 B2 | * | 7/2005 | Howlett et al. | ................ 433/173 |
| 7,694,812 B2 | * | 4/2010 | Bammerlin et al. | .......... 206/368 |
| 2003/0221977 A1 | | 12/2003 | Kumar et al. | |
| 2007/0193905 A1 | * | 8/2007 | Jemelin et al. | ................. 206/438 |
| 2009/0065387 A1 | | 3/2009 | Bammerline et al. | |

FOREIGN PATENT DOCUMENTS

| | | |
|---|---|---|
| DE | 10146 905 A1 | 7/2003 |
| DE | 10 2007 037593 A1 | 2/2004 |
| EP | 1 523 955 A | 10/2003 |
| WO | WO 98/53755 A | 12/1998 |
| WO | WO 00/02496 A | 1/2000 |

OTHER PUBLICATIONS

European Search Report dated May 1, 2010 in corresponding EP 09009674.4.

* cited by examiner

*Primary Examiner* — Luan K Bui
(74) *Attorney, Agent, or Firm* — Rissman Hendricks & Oliverio LLP

(57) ABSTRACT

Container for a medical instrument or an implant, in particular a dental instrument or a dental implant (14), the container having an outer housing part (16), and an inner housing part (18) which is movable relative to the outer housing part (16) from a closed position to an open position. The inner housing part (18) has a grip element (44) accessible from the outside. The container has a locking mechanism (22), which acts between the outer housing part (16) and the inner housing part (18), and an actuation of the grip element (44) causes an unlocking of the locking mechanism (22).

17 Claims, 5 Drawing Sheets

CONTAINER FOR A MEDICAL INSTRUMENT OR IMPLANT, IN PARTICULAR A DENTAL INSTRUMENT OR A DENTAL IMPLANT

FIELD OF THE INVENTION

The present invention relates to a container for a medical instrument or an implant, in particular a dental instrument or a dental implant.

BACKGROUND

There are basically two possible ways of supplying medical instruments or implants. One possibility is for such instruments or implants to be supplied in an unsterilized state, in which case it is essential that the instrument or implant, before being used on the patient, is sterilized by the surgeon or physician. Such a procedure, however, always entails the risk that the sterilization is carried out incompletely and under not entirely clean conditions, which can lead to later complications for the patient. Another possible way of supplying such medical instruments or implants is for them to be sterilized by the manufacturer before supply, and for the instrument or the implant then to be supplied in a sterile state for immediate use on the patient. A problem with this method is that, after the sterile barrier has been opened, the instruments often have to be inserted into a drive unit, as is the case with a drill, for example. Accordingly, implants in most cases have to be picked up with an auxiliary tool in order to use the latter to place the implant in the patient, as is the case, for example, with a dental implant, which is often screwed into the bone by means of a ratchet and of a screwing adapter. In doing so, it is necessary to ensure that, when the instrument or implant is being removed from the container and when it is being inserted into the drive instrument or the auxiliary tool, it is not subjected to chemical, biological or particulate contamination and thus rendered unsterile and its function impaired.

A corresponding container for medical instruments is known, for example, from DE 101 46 905. The latter discloses an instrument container which is of simple design and which permits easy and safe use, in particular handling, of a sterile medical instrument. The instrument container has a receiving part for the releasable mounting of at least one working part of the instrument, and a cap part which is secured releasably on said receiving part and which receives at least part of the shaft of the instrument. By this separation of the instrument container into two functional units, namely the receiving part and the cap part, it is possible for the manufacturer to supply the instrument in a sterile state and ready for use by the physician and for the instrument to be inserted into a drive unit or an auxiliary tool without contamination.

SUMMARY OF THE INVENTION

According to one or more embodiments of the present invention there is provided a container for a medical instrument or an implant, in particular a dental instrument or a dental implant, which container can be safely transported. Preferably the container is designed in such a way that the instrument or the implant has the fewest possible contact surfaces with the container, such that it is easier to sterilize the instrument or implant.

According to the present invention, the container for a medical instrument or an implant, in particular a dental instrument or a dental implant, has an outer housing part, and an inner housing part which is arranged inside the outer housing part. The inner housing part can be moved relative to the outer housing part from a closed position to an open position in order to close or open the container. The closed position is typically the position in which the container is transported and supplied, and the open position is typically the position in which the implant can be removed with the holder from the container. Moreover, the container is equipped with a locking mechanism which ensures that the inner housing part cannot be accidentally moved and thus shifted from the closed position to the open position by the movement of the inner housing part relative to the outer housing part. In order to unlock this locking mechanism, a grip element belonging to the inner housing part, and accessible from the outside, is actuated, which causes an unlocking of the locking mechanism. The unlocking can be effected, for example, by turning, clamping or screwing of the grip element.

The container is suitable in particular as a storage and transport container for dental implants, particularly preferably for completely ceramic dental implants. The container in this case contains an adapter and an implant. The adapter is arranged such that it is connected to the implant with a form fit. A holder is then inserted into the adapter, still in the closed position of the container, and connects itself to the implant with a form fit. The adapter serves to find the correct orientation of the holder in terms of rotation relative to the implant. Alternatively, it would of course also be possible to insert the holder into the container and connect it to the implant before transport/sterilization.

With its end lying inside the outer container, the inner container engages around resilient fingers or snap-action lips of the adapter which hold the implant. This increases the clamping force of the device during transport.

In another preferred embodiment of the container, the locking mechanism has a bayonet catch that acts between the outer housing part and the inner housing part.

Other embodiments of the locking mechanism are conceivable, for example a design in which cams or resilient fingers are mounted on the inner housing part and engage in corresponding groove-like recesses on the outer housing part and thus lock the outer housing part relative to the inner housing part. By manually pressing the cams or resilient fingers inward and at the same time turning the outwardly accessible grip element of the inner housing part, the cams or resilient fingers can be pressed out of their groove-like recesses and out of the locking position, which allows the inner housing part to move relative to the outer housing part and thus brings the inner housing part from the closed position to the open position. Alternatively, however, a screw closure would also be possible.

In a particularly preferred embodiment of the container, the adapter is arranged in such a way that the contact surface between the adapter and the implant is minimal. Sterilization of contact surfaces between two elements is made difficult by the fact that the sterilizing agent, for example EO gas, steam or $H_2O_2$, reaches microorganisms on these contact surfaces less effectively than it does in areas freely accessible to a liquid or a gas. Therefore, an advantage of minimizing the contact surface between the adapter and the implant is that the sterilization procedure is made easier. The smaller the contact surface, the smaller the sterilization surfaces that are difficult to sterilize completely, and it is thus possible to minimize the risks of side effects caused by poor or incomplete sterilization. The contact surfaces between adapter and implant are minimal by virtue of the fact that the adapter, in one end area thereof, has resilient fingers with supporting lugs which are in contact with the implant only via the bearing surfaces of the supporting lugs. Therefore, only a few areas of the implant are inaccessible to the sterilizing agent. Moreover, with the container according to the invention, there are no contact surfaces between the implant and the inner or outer housing part.

In a preferred embodiment, the manually separable arrangement of the adapter on one of the housing parts is achieved by means of a clamping device. This clamping device can either be mounted on the adapter or on the housing part. In a preferred embodiment, the clamping device is arranged on the front end of the inner housing part lying in the outer housing part. This clamping device encloses parts of the adapter that are preferably designed as resilient fingers. In this way, the implant or the medical instrument has no direct contact with a housing part of the container, as a result of which the sterilization procedure is again made easier and contamination of the implant by container materials is avoided. Moreover, the medical instrument or implant, in particular the dental instrument or the dental implant, is less susceptible to damage during transport if it has no contact surface with the container and, in the event of jolts, it does not strike against the container and suffer damage as a result.

In another preferred embodiment, one end of the holder, after insertion of the latter into the container, protrudes from the corresponding end face formed by the outer housing part, so as to facilitate access to the holder from outside the container. Ideally, the holder has a stem which serves for insertion into a screwing tool. In this way, the operator can use the screwing tool to remove the implant together with the holder and the adapter from the container without having to touch the implant, thereby maintaining optimal sterilization conditions. In doing so, the operator ideally engages the screwing tool into the stem of the holder with a click before the locking mechanism of the container is opened.

In another preferred embodiment, the inner housing part has a stop element which avoids the inner housing part being accidentally removed completely from the outer housing part. This means that the operator can easily remove the holder with the medical instrument or the implant without having to grip both the outer and also the inner housing part. The stop element can be a recess or a protuberance that strikes against an abutment or a receiving element of the outer housing part and thus avoids removal of the inner housing part. At the same time, a rotation of the inner housing part in the outer housing part can be avoided. In a preferred embodiment, the stop element latches in a mating element. A snap-action mechanism of this kind leads to the container being locked axially and in rotation in the open position.

The outer housing part, the inner housing part and the adapter are made of a biocompatible, sterilizable material, such that sterilization can be easily carried out. In a particularly preferred embodiment, the material of the outer housing part, of the inner housing part and of the adapter is, for example, titanium or plastic, stainless steel, ceramic or composite materials.

In another preferred embodiment of the container, the outer housing part and the inner housing part are dimensionally stable and preferably tubular. Moreover, the housing parts preferably have slit-like holes for better access of the sterilizing medium to the surface (implant, instrument). The dimensional stability has the effect that, particularly during transport, the medical instrument or implant, in particular the dental instrument or the dental implant, is optimally protected and escapes damage or contamination.

Instead of a two-part embodiment in which holder and adapter are two separate parts, a one-part design is also possible in which the adapter is an integral part of the holder. In this case, of course, the holder must already be in the container before transport, such that the integrated adapter is able to perform its transport safety function. However, the two-part embodiment is preferable.

In the two-part embodiment, the adapter can be secured on the holder. The adapter is equipped in an end area with resilient fingers, which have supporting lugs. The supporting lugs form bearing surfaces for the implant. The implant is supported and held on these bearing surfaces. The latter engage under the abutment of the implant and accordingly hold the implant with a form fit. This structure permits a secure holding of the implant, even though only a small surface of the implant is in contact with the adapter. This permits good sterilization of the implant.

In the one-part embodiment, the adapter is an integral part of the holder, that is to say the end area of the holder is equipped with the resilient fingers, which have supporting lugs. The supporting lugs in this case have the same function as in the two-part embodiment.

An important design feature of the adapter is that the bearing surface between the supporting lugs and the dental implant has a minimal surface area. The minimal contact surfaces between the adapter and the implant permit easy sterilization of the implant. Minimal signifies that the individual contact surfaces are less than 1 mm$^2$. The smaller the contact surface, the smaller the sterilization surfaces that are difficult to completely sterilize, and, accordingly, it is possible to minimize the risks of side effects caused by poor or incomplete sterilization of the implant.

In another preferred embodiment, the implant is a one-part implant, i.e. anchoring part and abutment are formed in one piece, and the implant is a ceramic implant. Ideally, the abutment of the implant is designed in such a way that the bearing surfaces of the supporting lugs of the adapter can engage under the shoulder surface of the abutment and thus hold the implant with a form fit.

BRIEF DESCRIPTION OF THE DRAWINGS

The invention is explained on the basis of an illustrative embodiment depicted in the drawings in which, in each case purely schematically:

FIG. 3b shows a detailed view of an adapter from FIG. 3a;

DETAILED DESCRIPTION

Figure 1:
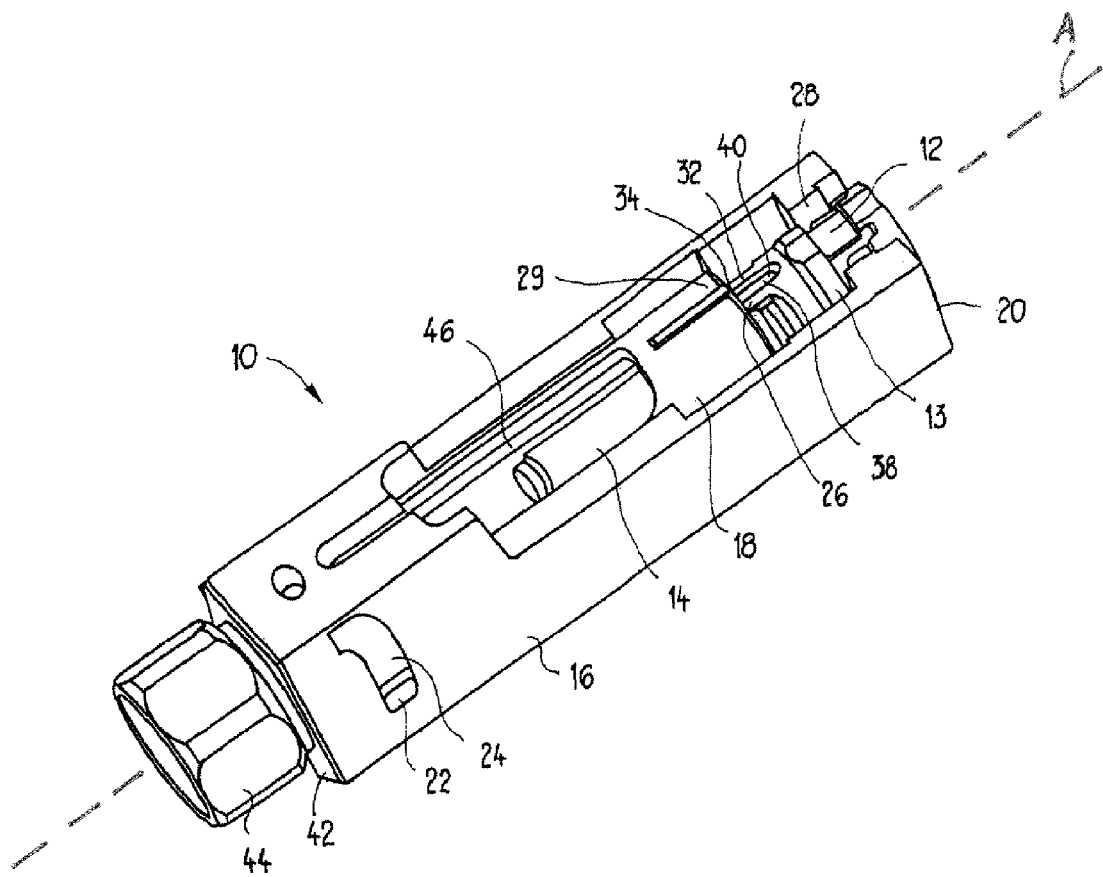
FIG. 1 shows a perspective view of a container for a medical instrument or an implant, in this embodiment for a dental implant, with the container located in a closed position.

FIG. 1 shows a perspective view of a container 10 with a holder 12 for a dental implant 14. The container 10 is formed by an outer housing part 16 and an inner housing part 18. The inner housing part 18 is arranged in the outer housing part 16. The inner housing part 18 is movable relative to the outer housing part 16, thereby allowing the container 10 to change from a closed position (shown in FIG. 1) to an open position (shown in FIG. 2). The shaft of the holder 12 for the dental implant 14 is accessible laterally from the outside at an end face 20 of the container 10 formed by the outer housing part 16, for example for the purpose of engaging the holder 12 and clamping it in a ratchet or another screwing tool. Moreover, the container 10 is equipped with a locking mechanism 22 which ensures that the inner housing part 18 cannot be moved accidentally and thus change from the closed position to the open position by the movement of the inner housing part 18 relative to the outer housing part 16. In the embodiment shown, the locking mechanism 22 acts between the outer housing part 16 and the inner housing part 18 and has a bayonet catch 24. The inner housing part 18 has a grip element 44, which is arranged outside the end face 42 of the outer housing part 16, said end face 42 lying remote from the end face 20. Actuation of the outwardly accessible grip element 44, by turning it, causes an unlocking of the locking mechanism 22. In this way, the inner housing part 18 can be moved relative to the outer housing part 16 to the open position by means of a movement parallel to the axis of the container 10. Alternatively, locking mechanisms are also conceivable that can be unlocked by means of clamping or screwing.

The outer housing part 16 and the inner housing part 18 can be tubular, for example. The end faces of the inner housing part 18 and of the outer housing part 16 can both be open.

A holder 12 is mounted on the adapter 13. At an end area 30 thereof, the adapter has resilient fingers 32, which are equipped with supporting lugs 34. These supporting lugs 34 form bearing surfaces 36 for the dental implant 14, in order to hold the latter. For this purpose, they ideally engage under the shoulder surfaces of the abutment of the implant and thus hold the implant with a form fit. The adapter serves to find the correct orientation of the holder in terms of rotation relative to the implant, when the holder is inserted into the adapter. The holder is held with a form fit to the abutment of the dental implant in a receiving area of the holder (not shown). Arranged between the supporting lugs 34 of the adapter 13, there are slit-like notches 38 which permit good sterilization.

The arrangement of the adapter 13 is effected by means of a clamping device 29, which is mounted on the inner housing part 18 at the end face remote from the grip element, and is designed such that the contact surface between the adapter 13 and the inner housing part 18 is minimal. The clamping device 29 presses the resilient fingers more strongly onto the implant 14 and, in the closed position of the container, provides additional safety during transport. In addition, this ensures that only the adapter 13 has contact surfaces with the container, namely with the inner housing part 18, whereas the dental implant 14 has no contact surfaces with the container.

In the present embodiment, adapter 13 and holder 12 are produced as two pieces. However, in an alternative embodiment, it is also conceivable for the adapter 13 to be an integral part of the holder 12 and, accordingly, for the holder 12 to be produced in one piece with the adapter 13.

In an alternative embodiment, the recess 28 in the outer housing part 16 is designed as a clamping or supporting device, thereby supporting the holder 12 upon insertion into the container in the closed state.

Figure 2:
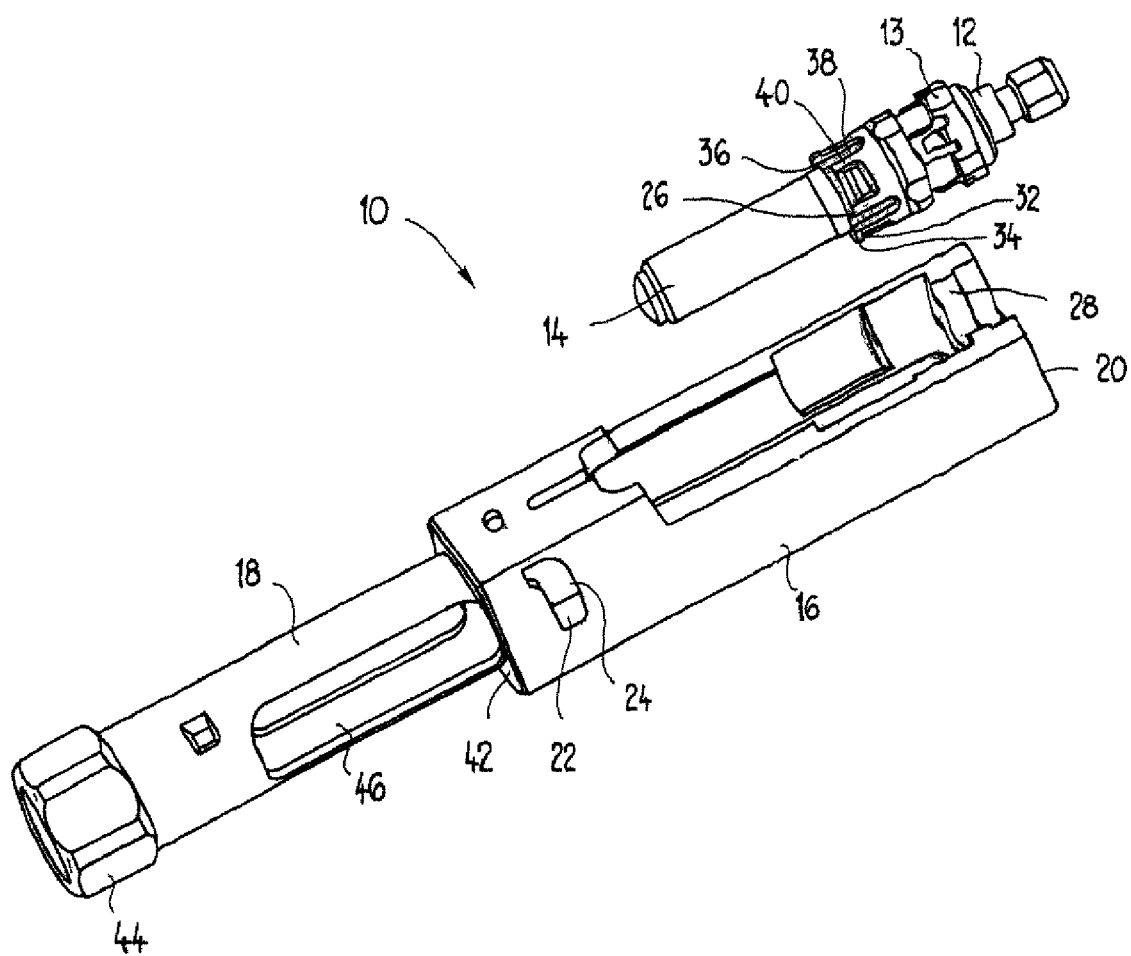
FIG. 2 shows a perspective view of the container from FIG. 1, with the container located in an open position.

FIG. 2 shows a perspective view of the container 10 from FIG. 1, with the container 10 being located not in the closed position as in FIG. 1, but instead in the open position. Moreover, the releasable arrangement between the adapter 13 and the inner housing part 18 is separated, and the holder 12, which together with the adapter 13 holds the dental implant 14, is removed from the interior of the container 10. Slit-like holes 46 can be clearly seen in the outer housing part 16 and inner housing part 18, which are preferably tubular.

These slit-like holes facilitate the sterilization procedure. At least one end face of the inner housing part 18 is preferably open, particularly preferably both end faces thereof are open. Ideally, both end faces of the outer housing part 16 are also open.

Figure 3A:
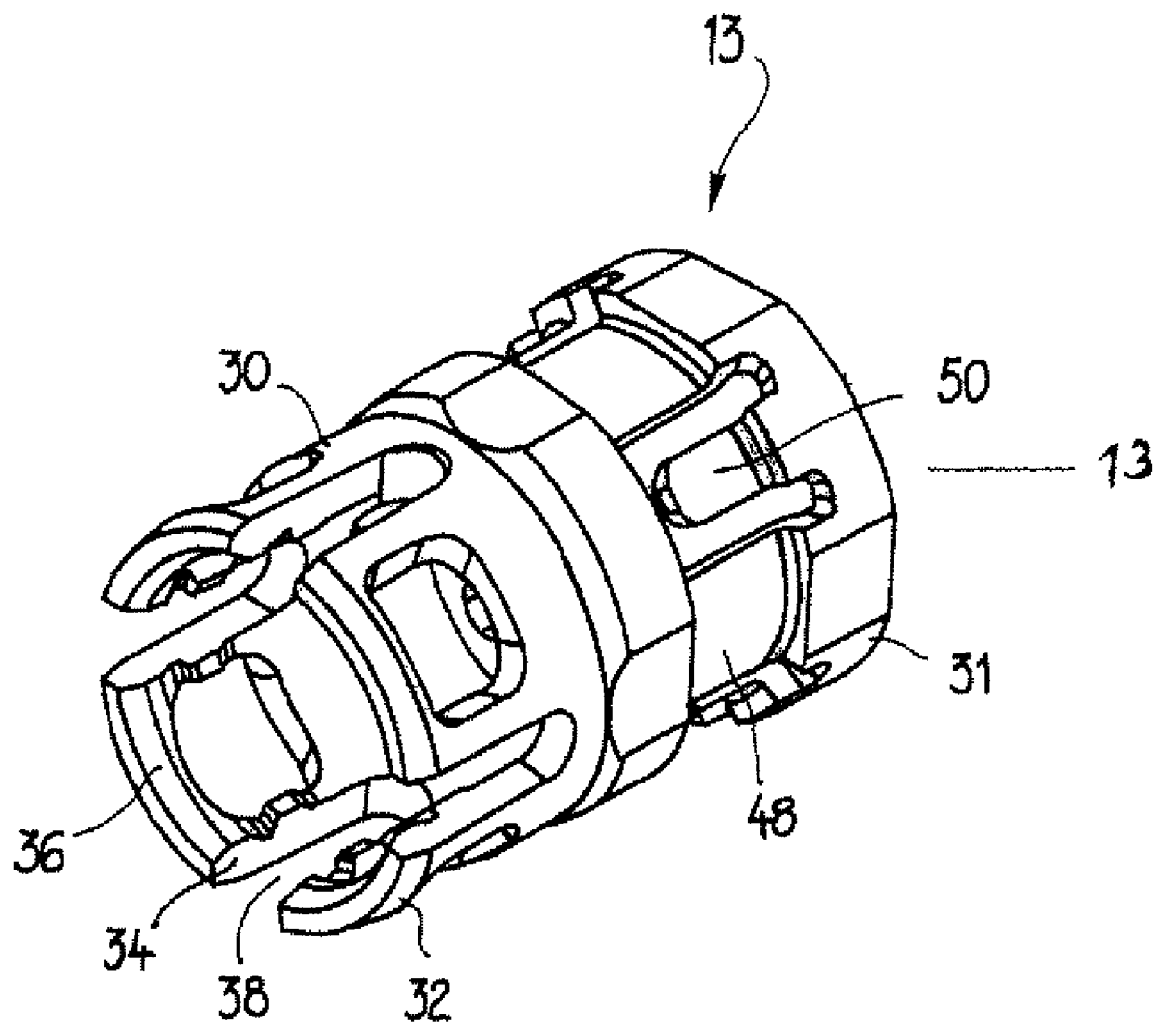
FIG. 3a shows a perspective detailed view of an adapter.

FIG. 3a shows a perspective detailed view of the adapter 13 shown in FIG. 1 and FIG. 2 for the dental implant 14. Resilient fingers 32, which are mounted on the end area 30 of the adapter and comprise supporting lugs 34, can be clearly seen.

Figure 3B:
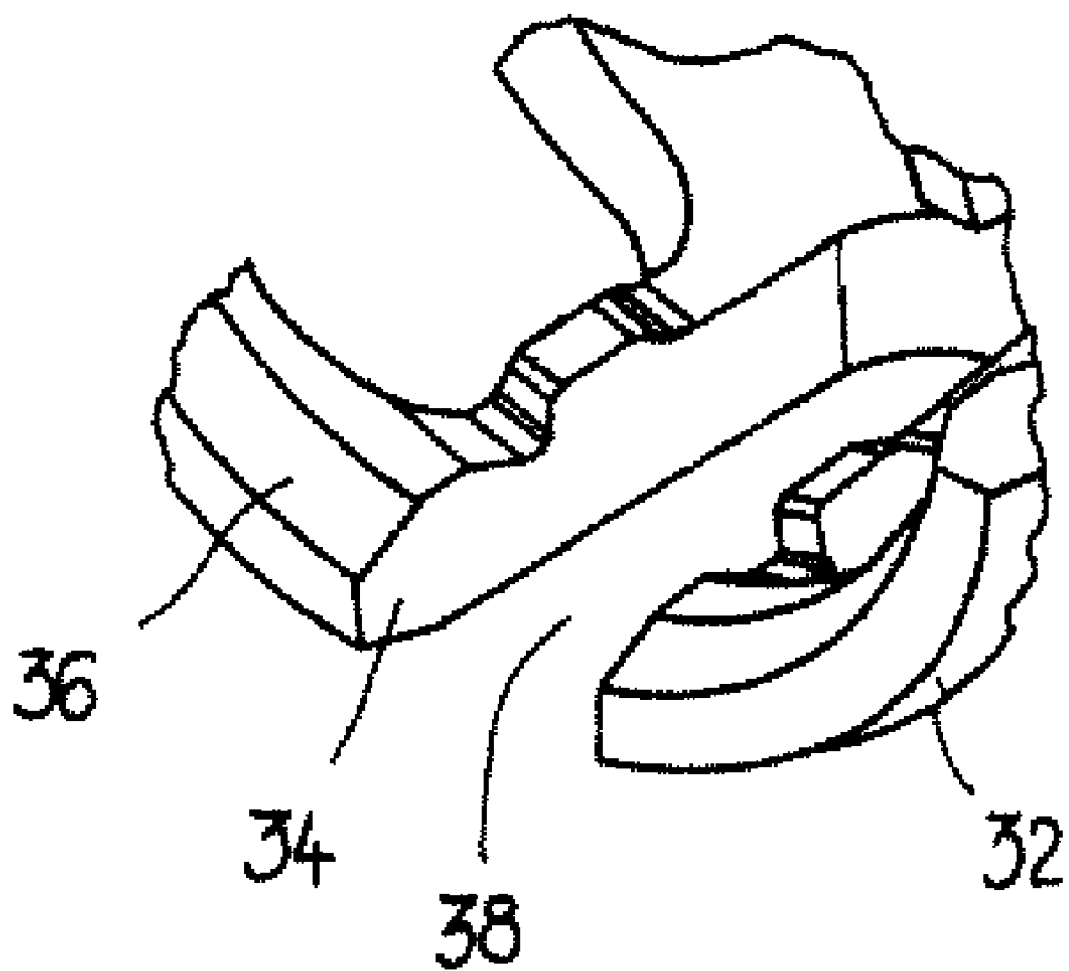

In FIG. 3b, these supporting lugs 34 are shown enlarged and in a detailed view. The supporting lugs 34 form bearing surfaces 36 for the dental implant 14. As is shown in FIG. 2, the dental implant 14 is supported and held on these bearing surfaces 36. The bearing surfaces 36 between the supporting lugs 34 and the dental implant 14 are designed such that they have a minimal surface area, in order to permit easy sterilization of the dental implant 14. Between the supporting lugs 34 of the adapter 13, there are slit-like notches 38. The supporting lugs 34 have cutouts in order to facilitate the sterilization of the dental implant 14 and to further reduce the contact surface between the dental implant 14 and the holder 12. In the embodiment shown in FIG. 3a, the adapter 13, in the end area 31 lying remote from the end area 30 of the adapter, has a notch-like recess 48 with further supporting fingers 50. This notch-like recess 48 with the further supporting fingers 50 forms part of the clamping device for mounting the adapter 13 on the holder 12. After the unit consisting of implant 14, adapter 13 and holder 12 has been removed from the container, the adapter 13 serves as an axial securing element between implant 14 and holder 12 and defines the axial release forces between these components. The axial release forces between the implant 14 and the adapter 13 are less than those between adapter 13 and holder 12. In this way, after the holder 12 has been withdrawn from the implant 14, the adapter 13 remains on the holder 12, that is to say holder 12 and adapter 13 remain together.

Figure 4:
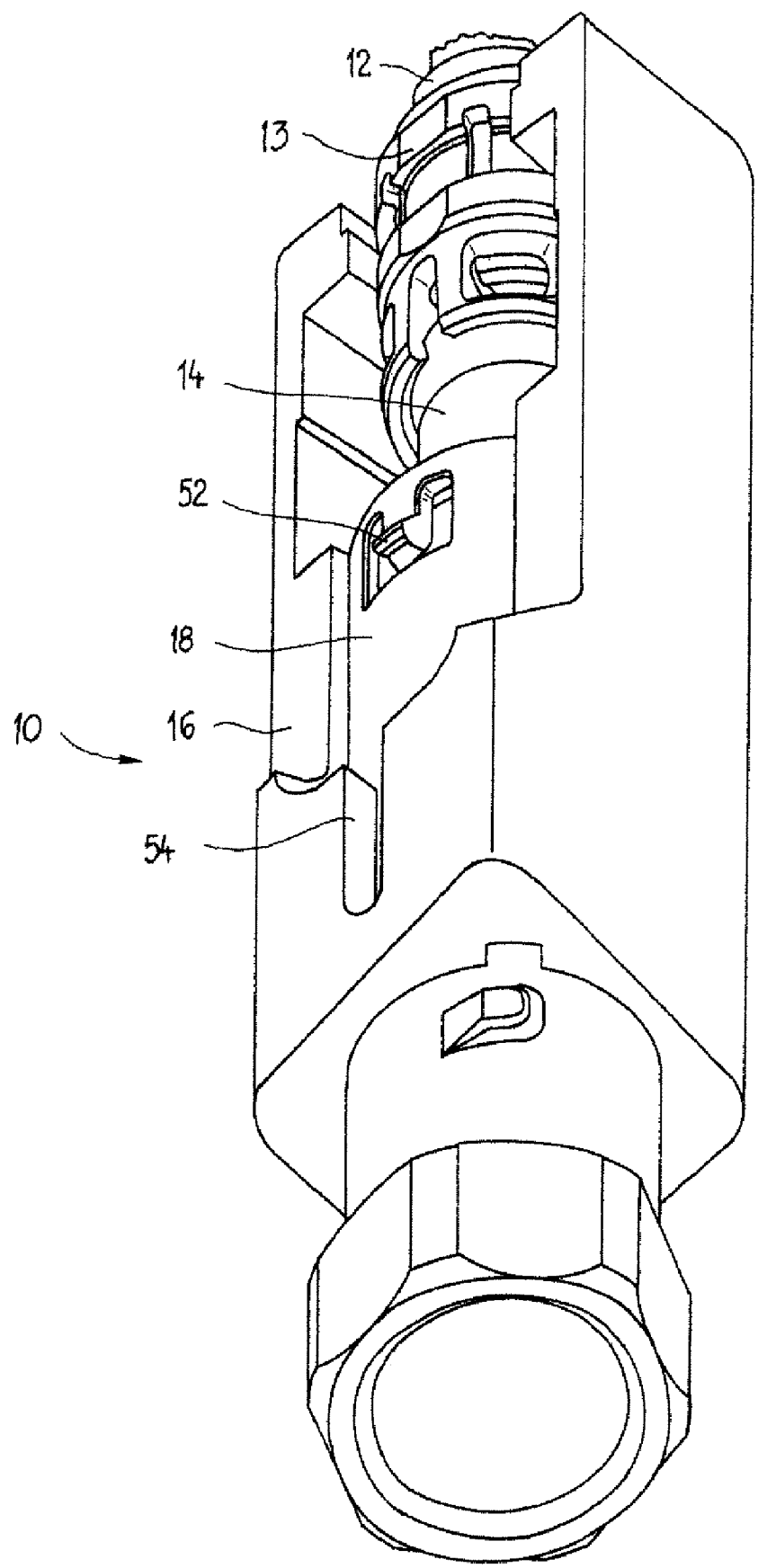
FIG. 4 shows a preferred embodiment with a stop element.

FIG. 4 shows another embodiment of the invention. The container 10 has an outer housing part 16 and an inner housing part 18, said inner housing part 18 being movable relative to the outer housing part 16. The adapter 13 for a dental implant 14 is still shown on the end face of the container 10. The inner housing part 18 has a stop element 52, which is designed to engage with an abutment surface or a recess 54 of the outer housing part 16 and thus avoid removal of the inner housing part 18 from the outer housing part 16. In its simplest configuration, the stop element 52 can be in the form of a protuberance, for example.

The invention claimed is:

1. A container for a medical instrument or an implant, in particular a dental implant, the container comprising:
   an outer housing part;
   an inner housing part which is arranged inside the outer housing part and is movable relative to the latter from a closed position to an open position, the inner housing part having a grip element accessible from outside the outer housing part;
   a locking mechanism which acts between the outer housing part and the inner housing part, the grip element having an actuation for unlocking of the locking mechanism;
   an implant; and
   an adapter, the adapter configured to receive a holder while the inner and outer housing parts are in the closed position, wherein the holder is configured to connect to the implant with a form fit.

2. The container as claimed in claim 1, wherein the locking mechanism is unlocked by turning, clamping or screwing of the grip element.

3. The container as claimed in claim 1, wherein the locking mechanism has a bayonet catch acting between the outer housing part and the inner housing part.

4. The container as claimed in claim 1, wherein the implant is a dental implant.

5. The container as claimed in claim 4, wherein the inner housing part has a clamping device for the adapter, which clamping device is mounted on an end of the inner housing part remote from the grip element.

6. The container as claimed in claim 5, wherein the adapter is arranged on the inner housing part in such a way that the contact surface between the adapter and the inner housing part is minimal.

7. The container as claimed in claim 6, wherein the adapter has resilient fingers and an end of the inner housing part arranged inside the outer housing part surrounds the resilient fingers of the adapter.

8. The container as claimed in claim 4, wherein the implant has only minimal contact surfaces with the adapter.

9. The container as claimed in claim 4, wherein the implant has no contact surfaces with either housing part of the container.

10. The container as claimed in claim 4, wherein the outer housing part, the inner housing part and the adapter are made of a biocompatible material.

11. The container as claimed in claim 1, wherein the outer housing part and the inner housing part are dimensionally stable.

12. The container as claimed in claim 1, wherein the outer housing part and the inner housing part are tubular and have slit-like holes for a sterilization procedure.

13. The container as claimed in claim 1, wherein both the inner housing part and the outer housing part are open at their respective end faces.

14. The container as claimed in claim 1, wherein the inner housing part has a stop element which is designed to engage with the outer housing part.

15. The container as claimed in claim 1, wherein the implant is a dental implant and the adapter is equipped, at an end area of said adapter, with resilient fingers which have supporting lugs to hold the dental implant on bearing surfaces that are formed by the supporting lugs, wherein the bearing surfaces between the supporting lugs and the dental implant have a minimal surface area, wherein said adapter, in an end thereof directed away from the end area with the resilient fingers, has a recess with further supporting lugs to hold the holder.

16. The container as claimed in claim 1, wherein the adapter holds a dental implant.

17. The container of claim 10, wherein the biocompatible material is titanium or plastic.

* * * * *